(12) United States Patent
Voegele et al.

(10) Patent No.: US 7,833,216 B2
(45) Date of Patent: Nov. 16, 2010

(54) FLUID PLUNGER ADHESIVE DISPENSER

(75) Inventors: James Walden Voegele, Cincinnati, OH (US); Mark S. Ortiz, Milford, OH (US); Christopher W. Widenhouse, Clarksville, OH (US); Fredrick E. Shelton, IV, New Vienna, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1043 days.

(21) Appl. No.: 11/557,619

(22) Filed: Nov. 8, 2006

(65) Prior Publication Data

US 2008/0105700 A1      May 8, 2008

(51) Int. Cl.
*A61M 31/00*   (2006.01)
*A61M 37/00*   (2006.01)

(52) U.S. Cl. .................................. 604/518; 604/82
(58) Field of Classification Search .............. 604/82, 604/537, 191, 83, 85, 518; 222/395, 1
See application file for complete search history.

(56) References Cited

U.S. PATENT DOCUMENTS

| | | | |
|---|---|---|---|
| 4,735,616 A | 4/1988 | Eibl et al. |
| 4,766,898 A | 8/1988 | Hardy et al. |
| 4,874,368 A | 10/1989 | Miller et al. |
| 5,004,469 A | 4/1991 | Palmieri et al. |
| 5,154,320 A | 10/1992 | Bolduc |
| 5,254,113 A | 10/1993 | Wilk |
| 5,312,333 A | 5/1994 | Churinetz et al. |
| 5,324,305 A | 6/1994 | Kanner |
| 5,372,585 A | 12/1994 | Tiefenbrun et al. |
| 5,443,481 A | 8/1995 | Lee |
| 5,474,540 A | 12/1995 | Miller et al. |
| 5,529,577 A | 6/1996 | Hammerslag |
| 5,582,596 A | 12/1996 | Fukunaga et al. |
| 5,605,541 A | 2/1997 | Holm |
| 5,718,711 A | 2/1998 | Berenstein et al. |
| 5,752,965 A | 5/1998 | Francis et al. |

(Continued)

FOREIGN PATENT DOCUMENTS

EP      0315222 B1      11/1992

(Continued)

OTHER PUBLICATIONS

Ikeda, et al.; "Auxiliary Tool for Device for Applying Adhesive on Living Tissue;" published in Japan [translated abstract for Patent Application No. JP2000286958]; Jun. 12, 2001.

(Continued)

*Primary Examiner*—Melba Bumgarner
(74) *Attorney, Agent, or Firm*—Frost Brown Todd LLC

(57) ABSTRACT

A system for dispensing an adhesive comprises a first dispenser, a second dispenser, and a conduit. The first dispenser contains an adhesive. The second dispenser comprises a fluid. The first dispenser and second dispenser are each in fluid communication with the conduit. The conduit has an opening. One or both of the first dispenser or the second dispenser is operable to dispense adhesive or fluid through the opening of the conduit. The system may be used to apply adhesive to the tissue of a patient in a precise and controlled manner.

1 Claim, 3 Drawing Sheets

U.S. PATENT DOCUMENTS

| | | |
|---|---|---|
| 5,759,169 A | 6/1998 | Marx |
| 5,759,171 A | 6/1998 | Coelho et al. |
| 5,814,022 A | 9/1998 | Antanavich et al. |
| 5,844,087 A | 12/1998 | Zimmerman et al. |
| 5,895,412 A | 4/1999 | Tucker |
| 5,928,611 A | 7/1999 | Leung |
| 5,981,621 A | 11/1999 | Clark et al. |
| 6,007,515 A | 12/1999 | Epstein et al. |
| 6,010,714 A | 1/2000 | Leung et al. |
| 6,055,828 A | 5/2000 | Rivera et al. |
| 6,099,807 A | 8/2000 | Leung |
| 6,113,571 A | 9/2000 | Zinger et al. |
| 6,143,352 A | 11/2000 | Clark et al. |
| 6,143,805 A | 11/2000 | Hickey et al. |
| 6,162,239 A | 12/2000 | Manhes |
| 6,174,919 B1 | 1/2001 | Hickey |
| 6,183,593 B1 | 2/2001 | Narang et al. |
| 6,206,905 B1 | 3/2001 | Holm et al. |
| 6,217,603 B1 | 4/2001 | Clark et al. |
| 6,228,051 B1 | 5/2001 | Trumbull |
| 6,234,994 B1 | 5/2001 | Zinger |
| 6,245,933 B1 | 6/2001 | Malofsky et al. |
| 6,280,399 B1 | 8/2001 | Rossin et al. |
| 6,283,933 B1 | 9/2001 | D'Alessio et al. |
| 6,302,898 B1 | 10/2001 | Edwards et al. |
| 6,306,243 B1 | 10/2001 | Clark et al. |
| 6,310,166 B1 | 10/2001 | Hickey et al. |
| 6,322,852 B1 | 11/2001 | Leung |
| 6,325,810 B1 | 12/2001 | Hamilton et al. |
| 6,340,097 B1 | 1/2002 | D'Alessio et al. |
| 6,352,704 B1 | 3/2002 | Nicholson et al. |
| 6,372,313 B1 | 4/2002 | D'Alessio et al. |
| 6,376,019 B1 | 4/2002 | Leung |
| 6,394,975 B1 | 5/2002 | Epstein |
| 6,394,982 B1 | 5/2002 | Ehrenfels |
| 6,398,797 B2 | 6/2002 | Bombard et al. |
| 6,412,639 B1 | 7/2002 | Hickey |
| 6,420,590 B1 | 7/2002 | Badejo et al. |
| 6,425,704 B2 | 7/2002 | Voiers et al. |
| 6,428,233 B1 | 8/2002 | Clark et al. |
| 6,428,234 B1 | 8/2002 | Bobo et al. |
| 6,432,084 B1 | 8/2002 | Levinson et al. |
| 6,433,096 B1 | 8/2002 | Hickey et al. |
| 6,439,789 B1 | 8/2002 | Balance et al. |
| 6,454,739 B1 | 9/2002 | Chang |
| 6,455,064 B1 | 9/2002 | Narang et al. |
| 6,458,095 B1 | 10/2002 | Wirt et al. |
| 6,461,361 B1 | 10/2002 | Epstein |
| 6,461,367 B1 | 10/2002 | Kirsch et al. |
| 6,464,663 B1 | 10/2002 | Zinger |
| 6,468,520 B1 | 10/2002 | Rowe et al. |
| 6,471,670 B1 | 10/2002 | Enrenfels et al. |
| 6,478,191 B1 | 11/2002 | D'Alessio et al. |
| 6,488,197 B1 | 12/2002 | Whitman |
| 6,488,650 B1 | 12/2002 | Epstein et al. |
| 6,488,944 B2 | 12/2002 | Narang |
| 6,491,201 B1 | 12/2002 | Whitman |
| 6,494,896 B1 | 12/2002 | D'Alessio et al. |
| 6,512,023 B1 | 1/2003 | Malofsky et al. |
| 6,527,749 B1 | 3/2003 | Roby et al. |
| 6,540,716 B1 | 4/2003 | Holm |
| 6,547,467 B2 | 4/2003 | Quintero |
| 6,565,840 B1 | 5/2003 | Clark et al. |
| 6,579,469 B1 | 6/2003 | Nicholson et al. |
| 6,585,967 B2 | 7/2003 | Narang et al. |
| 6,589,269 B2 | 7/2003 | Zhu et al. |
| 6,592,281 B2 | 7/2003 | Clark et al. |
| 6,595,940 B1 | 7/2003 | D'Alessio et al. |
| 6,602,496 B2 | 8/2003 | Hedgpeth et al. |
| 6,605,667 B1 | 8/2003 | Badejo et al. |
| 6,607,631 B1 | 8/2003 | Badejo et al. |
| 6,613,020 B1 | 9/2003 | Holm et al. |
| 6,616,019 B2 | 9/2003 | D'Alessio et al. |
| 6,620,846 B1 | 9/2003 | Jonn et al. |
| 6,637,967 B2 | 10/2003 | Bobo et al. |
| 6,666,873 B1 | 12/2003 | Cassell |
| 6,676,322 B1 | 1/2004 | Leung |
| 6,681,979 B2 | 1/2004 | Whitman |
| 6,695,199 B2 | 2/2004 | Whitman |
| 6,705,790 B2 | 3/2004 | Quintero et al. |
| 6,743,858 B2 | 6/2004 | Hickey et al. |
| 6,746,667 B2 | 6/2004 | Badejo et al. |
| 6,748,950 B2 | 6/2004 | Clark et al. |
| 6,764,467 B1 | 7/2004 | Roby et al. |
| 6,767,552 B2 | 7/2004 | Narang |
| 6,779,657 B2 | 8/2004 | Mainwaring et al. |
| 6,783,514 B2 | 8/2004 | Tovey et al. |
| 6,802,416 B1 | 10/2004 | D'Alessio et al. |
| 6,802,822 B1 | 10/2004 | Dodge |
| 6,811,341 B2 | 11/2004 | Crane |
| D500,085 S | 12/2004 | Cotter et al. |
| 6,837,027 B2 | 1/2005 | Hickey |
| 6,863,660 B2 | 3/2005 | Marx |
| 6,884,232 B1 | 4/2005 | Hagmann et al. |
| 6,896,684 B2 | 5/2005 | Monassevitch et al. |
| 6,896,838 B2 | 5/2005 | D'Alessio |
| 6,921,381 B2 | 7/2005 | Spero et al. |
| 6,942,875 B2 | 9/2005 | Hedgpeth |
| 6,960,040 B2 | 11/2005 | D'Alessio et al. |
| 7,037,344 B2 | 5/2006 | Kagan et al. |
| 7,610,943 B2 * | 11/2009 | Nollert et al. ............... 141/107 |
| 2002/0012678 A1 | 1/2002 | Narang |
| 2002/0037310 A1 | 3/2002 | Jonn et al. |
| 2002/0048480 A1 | 4/2002 | D'Alessio et al. |
| 2002/0055573 A1 | 5/2002 | Malofsky et al. |
| 2002/0065336 A1 | 5/2002 | Hickey et al. |
| 2002/0119184 A1 | 8/2002 | Nicholson et al. |
| 2002/0147462 A1 | 10/2002 | Mair et al. |
| 2002/0156203 A1 | 10/2002 | Hickey et al. |
| 2002/0157675 A1 | 10/2002 | Clark et al. |
| 2002/0165483 A1 | 11/2002 | Miller et al. |
| 2002/0173770 A1 | 11/2002 | Flory et al. |
| 2002/0176732 A1 | 11/2002 | Quintero et al. |
| 2002/0176733 A1 | 11/2002 | Clark et al. |
| 2002/0185396 A1 | 12/2002 | Mainwaring et al. |
| 2002/0192011 A1 | 12/2002 | Bobo et al. |
| 2002/0192107 A1 | 12/2002 | Hickey |
| 2003/0007826 A1 | 1/2003 | Badejo et al. |
| 2003/0007946 A1 | 1/2003 | Narang et al. |
| 2003/0007947 A1 | 1/2003 | Narang |
| 2003/0007948 A1 | 1/2003 | Hedgpeth |
| 2003/0007949 A1 | 1/2003 | Hedgpeth et al. |
| 2003/0015557 A1 | 1/2003 | D'Alessio et al. |
| 2003/0031499 A1 | 2/2003 | Heard et al. |
| 2003/0032833 A1 | 2/2003 | Badejo et al. |
| 2003/0039781 A1 | 2/2003 | D'Alessio et al. |
| 2003/0044219 A1 | 3/2003 | Quintero |
| 2003/0060380 A1 | 3/2003 | Ayarza et al. |
| 2003/0063944 A1 | 4/2003 | Leung |
| 2003/0080151 A1 | 5/2003 | D'Alessio et al. |
| 2003/0082116 A1 | 5/2003 | Badejo et al. |
| 2003/0096069 A1 | 5/2003 | D'Alessio |
| 2003/0149128 A1 | 8/2003 | Malofsky et al. |
| 2003/0181964 A1 | 9/2003 | Sharkey et al. |
| 2003/0202956 A1 | 10/2003 | Clark et al. |
| 2004/0026282 A1 | 2/2004 | D'Alessio et al. |
| 2004/0059283 A1 | 3/2004 | Kirwan et al. |
| 2004/0111115 A1 | 6/2004 | Maw |
| 2004/0120849 A1 | 6/2004 | Stewart et al. |
| 2004/0137067 A1 | 7/2004 | Narang et al. |
| 2004/0143290 A1 | 7/2004 | Brightbill |
| 2004/0151688 A1 | 8/2004 | Sherbondy et al. |
| 2004/0190975 A1 | 9/2004 | Goodman et al. |
| 2004/0223932 A1 | 11/2004 | Hedgpeth et al. |

| | | | |
|---|---|---|---|
| 2004/0223946 A1 | 11/2004 | Kidd et al. | |
| 2004/0234578 A1 | 11/2004 | Chen et al. | |
| 2004/0254561 A1 | 12/2004 | Stenton | |
| 2005/0033328 A1 | 2/2005 | Laufer et al. | |
| 2005/0042266 A1 | 2/2005 | Narang | |
| 2005/0047846 A1 | 3/2005 | Narang et al. | |
| 2005/0070935 A1 | 3/2005 | Ortiz | |
| 2005/0145671 A1 | 7/2005 | Viola | |
| 2005/0147457 A1 | 7/2005 | Badejo et al. | |
| 2005/0175395 A1 | 8/2005 | Quintero et al. | |
| 2005/0182443 A1 | 8/2005 | Jonn et al. | |
| 2005/0184121 A1 | 8/2005 | Heinrich | |
| 2005/0220849 A1 | 10/2005 | Hickey | |
| 2005/0228446 A1 | 10/2005 | Mooradian et al. | |
| 2005/0230453 A1 | 10/2005 | Viola | |
| 2005/0256446 A1 | 11/2005 | Criscuolo et al. | |
| 2006/0009099 A1 | 1/2006 | Jonn et al. | |

FOREIGN PATENT DOCUMENTS

| | | |
|---|---|---|
| EP | 0716833 A2 | 6/1996 |
| EP | 0648510 B1 | 11/1998 |
| EP | 0669100 B1 | 11/1998 |
| EP | 1078600 A2 | 2/2001 |
| EP | 1159081 A1 | 12/2001 |
| EP | 1381321 A2 | 1/2004 |
| EP | 1113839 B1 | 11/2004 |
| EP | 1073484 B1 | 8/2005 |
| EP | 1411836 B1 | 10/2005 |
| JP | 10262986 | 10/1998 |
| JP | 2000217830 | 8/2000 |
| JP | 2001157716 | 6/2001 |
| JP | 2001190558 | 7/2001 |
| JP | 2002233581 | 8/2002 |
| JP | 2003126268 | 5/2003 |
| JP | 2005028009 | 2/2005 |
| JP | 2005169125 | 6/2005 |
| WO | WO 92/09651 | 6/1992 |
| WO | WO 95/31137 A1 | 11/1995 |
| WO | WO 98/41154 A1 | 9/1998 |
| WO | WO 99/17833 A1 | 4/1999 |
| WO | WO 99/30629 | 6/1999 |
| WO | WO 01/12257 | 2/2001 |
| WO | WO 01/24869 A1 | 4/2001 |
| WO | WO 01/62158 A2 | 8/2001 |
| WO | WO 01/62162 A1 | 8/2001 |
| WO | WO 01/62333 A1 | 8/2001 |
| WO | WO 02/067785 A2 | 9/2002 |
| WO | WO 03/088845 | 10/2003 |

OTHER PUBLICATIONS

Ikeda, et al.; "Device for Applying Organism Tissue Adhesive;" published in Japan [translated abstract for Patent Application No. JP2000320375]; Jul. 17, 2001.

Gomibuchi, Makoto; "Medical Adhesive Applicator;" published in Japan [translated abstract for Patent Application No. JP11023146]; Aug. 8, 2000.

Ikeda, et al.; "Organism-Tissue Adhesive Applicator;" published in Japan [translated abstract for Patent Application No. JP2001033756]; Aug. 20, 2002.

Ikeda, et al.; "Biological Tissue Adhesive Applicator;" published in Japan [translated abstract for Patent Application No. JP2001323890]; May 7, 2003.

Arikawa, Seiki; "Biological Tissue Adhesive Applicator;" published in Japan [translated abstract for Patent Application No. JP2003273091]; Feb. 3, 2005.

Keller, Wilhelm A.; "Applicator for Dispensing Appliance;" published in Japan [translated abstract for Patent Application No. JP2004358509]; Jun. 30, 2005.

Sasaki, Hiroshi; "Adhesive Agent Applicator for Surgical Operation;" published in Japan [translated abstract for Patent Application No. JP09076817]; Oct. 6, 1998.

\* cited by examiner

FLUID PLUNGER ADHESIVE DISPENSER

BACKGROUND

Biosurgical adhesives have been used in a variety of ways in various medical procedures. An exemplary adhesive is disclosed in U.S. Pub. No. 2004/0190975, the disclosure of which is incorporated by reference herein. Similarly, a variety of devices and techniques have been used to deliver adhesives at various sites. While several systems and methods have been made and used for delivering adhesives, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
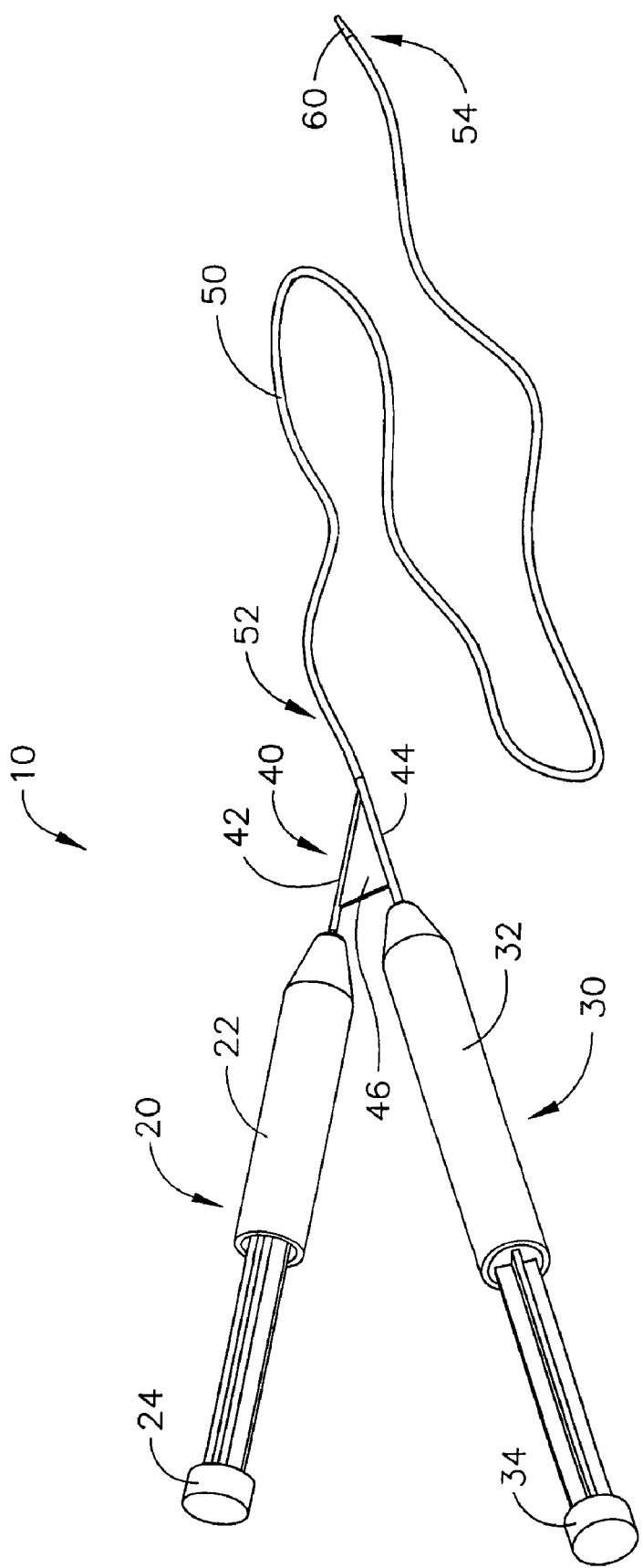
FIG. 1 depicts a perspective view of an exemplary adhesive delivery system.

As shown in FIG. 1, an exemplary adhesive delivery system (10) comprises a first syringe (20), a second syringe (30), a junction member (40), and a tube (50). Each of syringes (20, 30) is coupled with junction member (40), which is further coupled with the proximal end (52) of tube (50). A tip (60) is secured to the distal end (54) of tube (50).

Syringes (20, 30) each comprise a respective barrel (22, 32) and plunger (24, 34). In the present example, each of syringes (20, 30) comprises a standard commercially available syringe, without a needle attached, though any suitable alternatives may be used. As shown, each syringe (20, 30) is coupled with junction member (40), and each syringe (20, 30) is further in fluid communication with junction member (40). As will be described in greater detail below, in an exemplary use of adhesive delivery system (10), barrel (22) of first syringe (20) contains an adhesive material; while barrel (32) of second syringe (30) contains a fluid (72). While syringes (20, 30) are described herein as being used to dispense an adhesive material and a fluid, it is contemplated that a variety of alternative structures and devices may be used to dispense either or both of an adhesive material and a fluid.

Junction member (40) of the present example comprises a first channel (42), which is in fluid communication with a second channel (44). In one embodiment, first and second channels (42, 44) each comprise a leur lock type of feature (not shown), each of which are configured to mate with complimentary leur lock features (not shown) of first and second syringes (20, 30). Alternatively, any other suitable interface between syringes (20, 30) and conduits (42, 44) may be used. First and second channels (42, 44) form a generally "V"-like configuration in the present example. However, it will be appreciated that first and second channels (42, 44) may have any other suitable configuration (e.g., "T"-shaped, etc.). As is also shown, a web (46) is provided between first and second channels (42, 44). In this example, web (46) is substantially rigid, though web (46) may have other properties. It will also be appreciated that web (46) is optional, and that any suitable alternative may be used, and/or that web (46) may be omitted altogether.

Figure 2:
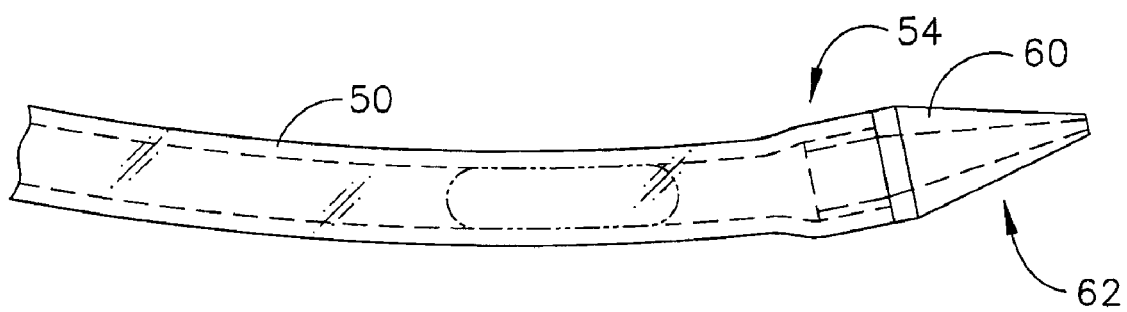
FIG. 2 depicts a partial view of a distal end of the adhesive delivery system of FIG. 1.
Figure 3:
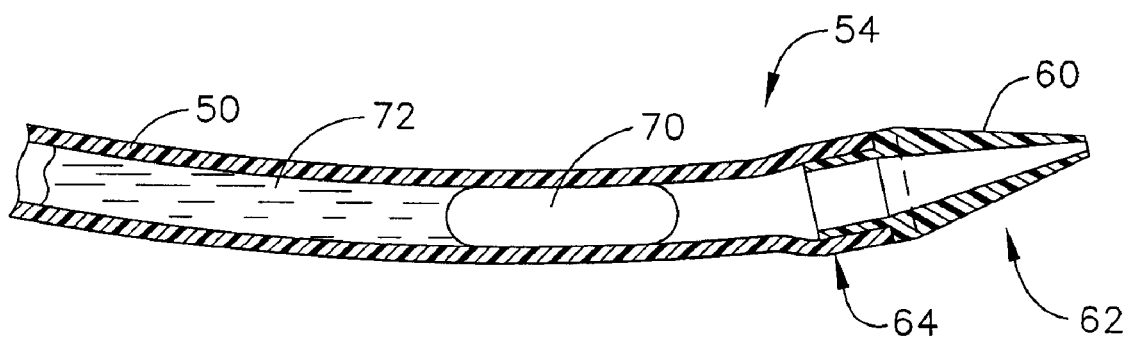
FIG. 3 depicts a cross-sectional view of the distal end shown in FIG. 2.
Figure 4:
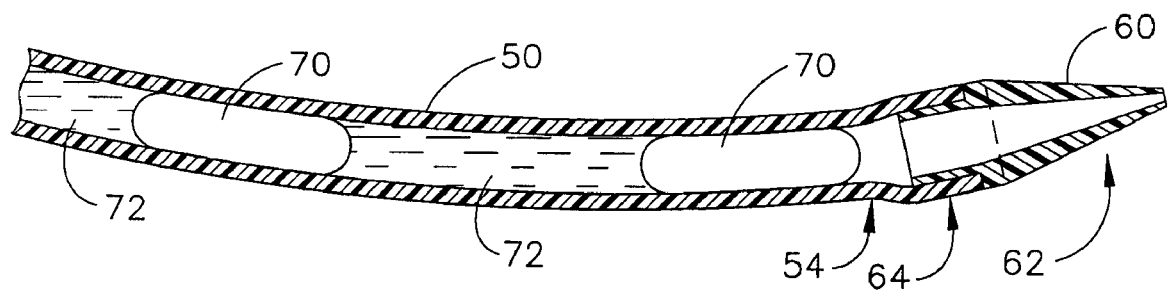
FIG. 4 depicts a cross-sectional view of the distal end shown in FIG. 2, with two adhesive plugs disposed therein.

Proximal end (52) of tube (50) is secured to second channel (44), distal of the junction of first and second channels (42, 44), and tube (50) is further in fluid communication with second channel (44). Tube (50) comprises a flexible, transparent material in the present example, though it will be appreciated that tube (50) may have any other suitable properties. Tip (60) is secured to distal end (54) of tube (50), and is further in fluid communication with tube (50). As shown in FIGS. 2-4, tip (60) comprises a generally tapered portion (62) and a generally cylindrical portion (64). Generally cylindrical portion (64) is inserted in distal end (54) of tube (50). Of course, tip (60) may have any of a variety of alternative configurations, and may engage with tube (50) in any other suitable fashion.

The adhesive delivery system (10) of the present example is configured to deliver an adhesive through tip (60) via actuation of plungers (24, 34) of syringes (20, 30). An exemplary use is shown in FIGS. 2-4, where an adhesive plug (70) is shown within tube (50). Adhesive plug (70) may comprise a cyanoacrylate, an isocyanate, or any other suitable substance. Adhesive plug (70) is urged distally through tube (50) by a fluid (72), such as sterile water, saline, or any other suitable fluid (72). In the present example, adhesive plug (70) is immiscible in fluid (72). Adhesive plug (70) and fluid (72) are further provided in different colors, thereby providing visual feedback of the longitudinal position of adhesive plug (70) in tube (50). Alternatively, adhesive plug (70) and fluid (72) may be the same color or similar colors, or may be contrasted in any suitable way. It will be appreciated that fluid (72) may act as a plunger to drive adhesive plug (70) along tube (50). In other words, adhesive plug (70) may be advanced distally through tube (50) by a user actuating plunger (34).

As is shown in FIG. 4, a plurality of adhesive plugs (70) may be provided within tube (50). Where a plurality of adhesive plugs (70) are provided within tube (50), fluid (72) may be provided between adhesive plugs (70).

It will be appreciated that each adhesive plug (70) may be created by a user actuating plunger (24) to introduce adhesive material residing in barrel (22) to junction member (40) and/or tube (50). When a desired quantity of adhesive material has been so introduced, the user may stop actuating plunger (24) and may start actuating plunger (34) to distally force fluid (72) behind the adhesive material, thereby separating an adhesive plug (70) portion from the remainder of adhesive material within first channel (40). It will therefore be appreciated that adhesive plugs (70) may be provided in any size/amount desired by the user as a function of plunger (24, 34) manipulation. Adhesive plugs (70) may also be introduced at any point along the stream of fluid (72).

As noted above, fluid (72) of the present example comprises a sterile water or saline. However, suitable alternatives for fluid (72) may include any media that is immiscible with adhesive plug (70) (e.g., liquid, air, gel, etc.), and may comprise any suitable drug, sclerosing agent, necrosing agent, coagulant, ablation agent, image enhancing agents such as ultrasound, CT, MRI, PET, X-Ray (radiographic), sealants, or radiopharmaceutical. Other suitable alternatives for fluid (72) will be apparent to those of ordinary skill in the alt. It will also be appreciated that fluid (72) may comprise more than one type of fluid and/or material. Similarly, adhesive plug (70) may be substituted with any suitable fluid and/or material, including but not limited to the above-listed alternatives for fluid (72).

In one exemplary use, adhesive delivery system (10) is used to deliver tissue glue, which is provided by adhesive plug (70), in measured quantities. For instance, adhesive delivery system (10) may be used to adhere portions of tissue of a patient together. However, adhesive delivery system (10) may be used in a variety of other procedures and/or to deliver a variety of materials other than adhesive plugs (70). Suitable alternative uses for adhesive delivery system (10) will be apparent to those of ordinary skill in the art.

It will be appreciated that either or both of syringes (20, 30) may be selectively coupled with junction member (40), such that either or both of syringes (20, 30) may be removed from junction member (40) during a procedure of applying adhesive. For instance, syringe (20) may be used initially to provide an adhesive plug (70), and may then be removed from junction member (40). A replacement syringe (not shown) containing some other substance (e.g., an initiator, curing agent, a different adhesive, etc.) may then be selectively coupled with first channel (42). Such a replacement syringe could then be used to introduce the other substance to tube (50) behind a suitable amount of fluid (72). The other substance may then be advanced through tube (50) using additional fluid (72). Other suitable substances that may be introduced to tube (50) by either syringe (20, 30) will be apparent to those of ordinary skill in the art; as will other uses for embodiments described herein, structural variations of embodiments described herein, and substitutes and variations of components described herein.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. the sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A method of applying an adhesive to the tissue of a patient during a surgical procedure, the method comprising:
   (a) providing an adhesive dispensing system, wherein the adhesive dispensing system comprises:
      (i) a first dispenser containing a biosurgical adhesive, wherein the adhesive comprises one of cyanoacrylate or isocyanate;
      (ii) a second dispenser containing a fluid immiscible with said adhesive, said fluid comprising a drug, sclerosing agent, necrosing agent, coagulant, ablation agent, image enhancing agents, sealants, radiopharmaceutical, or combinations thereof, wherein said fluid is of a different color than said biosurgical adhesive;
      (iii) a conduit comprising a substantially transparent, flexible tube, wherein each of the first dispenser and the second dispenser is in fluid communication with the conduit, wherein the conduit comprises an opening, wherein the one or both of the first dispenser or second dispenser is operable to dispense adhesive or fluid through the opening of the conduit;
   (b) using the first dispenser to dispense an amount of adhesive into the conduit;
   (c) using the second dispenser to dispense an amount of fluid into the conduit, wherein the dispensed fluid is urged against the dispensed adhesive;
   (d) using the dispensed fluid to urge the dispensed adhesive through the conduit; and
   (e) applying the dispensed adhesive to the tissue of the patient during the surgical procedure.

* * * * *